US 6,706,016 B2

(12) United States Patent
Cory et al.

(10) Patent No.: US 6,706,016 B2
(45) Date of Patent: Mar. 16, 2004

(54) NERVE STIMULATOR OUTPUT CONTROL NEEDLE WITH DEPTH DETERMINATION CAPABILITY AND METHOD OF USE

(75) Inventors: Joan M. Cory, Bozeman, MT (US); Philip C. Cory, Bozeman, MT (US)

(73) Assignee: CKM Diagnostics, Inc., Bozeman, MT (US)

(*) Notice: Subject to any disclaimer, the term of this patent is extended or adjusted under 35 U.S.C. 154(b) by 0 days.

(21) Appl. No.: 09/989,206

(22) Filed: Nov. 21, 2001

(65) Prior Publication Data
US 2002/0065481 A1 May 30, 2002

Related U.S. Application Data
(60) Provisional application No. 60/253,064, filed on Nov. 24, 2000.

(51) Int. Cl.[7] ............ A61M 5/00; A61N 1/30; A61N 1/00
(52) U.S. Cl. ............ 604/117; 604/21; 607/118
(58) Field of Search ............ 604/21, 500, 501, 604/506, 117; 607/3, 115, 116, 118; 606/44

(56) References Cited

U.S. PATENT DOCUMENTS

| | | | | |
|---|---|---|---|---|
| 4,299,230 A | * | 11/1981 | Kubota | 128/630 |
| 4,515,168 A | | 5/1985 | Chester et al. | 128/741 |
| 5,306,236 A | | 4/1994 | Blumenfeld et al. | 604/21 |
| 5,358,514 A | * | 10/1994 | Schulman et al. | 607/61 |
| 5,389,069 A | * | 2/1995 | Weaver | 604/21 |
| 5,725,514 A | * | 3/1998 | Grinblat et al. | 604/294 |
| 5,830,151 A | * | 11/1998 | Hadzic | 600/554 |
| 5,853,373 A | * | 12/1998 | Griffith et al. | 600/554 |
| 5,993,434 A | * | 11/1999 | Dev et al. | 604/501 |
| 6,009,347 A | * | 12/1999 | Hofmann | 604/21 |
| 6,298,256 B1 | * | 10/2001 | Meyer | 600/373 |
| 6,325,764 B1 | * | 12/2001 | Griffith et al. | 600/554 |
| 6,391,005 B1 | * | 5/2002 | Lum et al. | 604/117 |

OTHER PUBLICATIONS

"A National Survey on Practice Patterns in the Use of Peripheral Nerve Stimulators in Regional Anesthesia", JD Vloka et al., The Internet Journal of Anesthesiology, vol. 3, No. 4, 1999.

"Nerve Stimulators for Nerve Location—Are They All the Same?", C. N. Barthram, Anaesthesia, vol. 52, 1997, pp. 761–764.

* cited by examiner

*Primary Examiner*—Sharon Kennedy
(74) *Attorney, Agent, or Firm*—McDermott, Will & Emery

(57) ABSTRACT

An improved nerve stimulator needle which allows for improved ease of use and efficacy in the performance of targeted drug delivery to nerve. A variable control mechanism is contained in a housing to which a needle is attached and several electrical conductors are attached. The housing contains an embedded fluid path through which a syringe is attached to the needle. The variable control mechanism and the housing allows for positioning the needle and applying current to the needle with the same hand. The needle may also contain a linear resistive coating that enables the determination of the depth of the needle by determining the resistance of the length of the needle above the skin surface of a patient. Another embodiment of the needle may include an optical variable control mechanism.

28 Claims, 11 Drawing Sheets

NERVE STIMULATOR OUTPUT CONTROL NEEDLE WITH DEPTH DETERMINATION CAPABILITY AND METHOD OF USE

This application claims priority to U.S. provisional application 60/253,064 filed on Nov. 24, 2000, which is herein incorporated by reference.

TECHNICAL FIELD

This invention relates to a nerve-stimulating needle with fingertip control of stimulator current output and visual as well as electrical depth determination ability.

BACKGROUND OF THE INVENTION

Anesthesiologists commonly use nerve stimulators and insulated needles for the purpose of locating peripheral nerves, or nerve plexuses, for the performance of regional anesthesia procedures. This procedure is discussed in Vloka J D et al., "A National Survey On Practice Patterns In The Use Of Peripheral Nerve Stimulators In Regional Anesthesia," The Internet Journal of Anesthesiology, Vol. 3, No. 4, 1999. In addition to targeting local anesthetic delivery for regional anesthesia, the use of nerve stimulators reduces the potential for nerve injury since direct contact with the nerve is not required for performance of the anesthetic. This is in contrast to the alternative method of seeking paresthesias to confirm needle position. Paresthesias are provoked by directly disturbing the nerve. If such needle to nerve contact can be avoided, direct needle trauma should be reduced.

The available nerve stimulators have differing output characteristics. The shape of the pulse is typically square or nearly so. The pulse widths vary from 40 microseconds ($\mu s$) to 2 milliseconds (ms). Frequency selections for these stimulators range from 1.0 Hertz (Hz) to 100 Hz, in step gradations rather than continuously. Stimulators that are manufactured specifically for regional anesthesia applications typically do not have frequency options greater than 5 Hz. The stimulators that serve as both nerve stimulators and neuromuscular blockade monitors offer higher frequency choices, typically 50 and 100 Hz. These stimulators are discussed in Barthram CN, "Nerve Stimulators For Nerve Location—Are They All The Same?," *Anaesthesia*, Vol. 52, 1997, pp. 761–764.

The needles used for stimulator assisted regional anesthesia typically have a molded plastic hub that contains both a connection to plastic tubing and a wire attached to the metal needle imbedded in the hub. This wire, when connected to a source, supplies electrical current to the needle with appropriate output characteristics for generation of action potentials in axons. Use of this equipment requires a means for holding the needle assembly, adjusting the output current, and injecting medication. This is awkward for a single user to accomplish and usually requires the presence of an assistant.

The commercially available nerve stimulators offer two methods of controlling the current output from the nerve stimulator instrument to a nerve stimulator needle. The first method is by hand-operated dials on the face of the nerve stimulator instruments. In this method, it is difficult for a single operator to insert and position the needle in the patient, control the current supplied the nerve stimulator needle, and inject the medication in the patient.

The second method is by a foot-operated pedal connected via a cable to the nerve stimulator instrument. An output source with foot-pedal control, such as described in U.S. Pat. No. 5,830,151 to Hadzic, necessitates a multiplicity of wires connecting pieces of equipment together. In the environment of an operating room where a multiplicity of electrical cables already exists, any equipment that adds additional cables spread out across the floor or tables and carts represents increased hazard for stumbling and consequent injury. Also, efficiency of movement is highly prized in the operating room environment. When an anesthetic procedure is completed, the operating room personnel move rapidly to begin the surgical positioning and prepping. Often, the anesthesiologist is in the position of gathering up equipment used for a procedure, and either disposing of it or placing it on a cart for subsequent storage. Tangles of cables and wires complicate this process and have a tendency to increase the clutter surrounding anesthesia machines and carts.

U.S. Pat. No. 4,515,168 to Chester et al. discloses to clamp a nerve stimulator and locating device onto a syringe. As the entire nerve stimulator device is clamped onto the syringe, the unit is a long and clumsy assembly, which is difficult to maneuver. Moreover, the device disclosed by Chester does not allow for one-handed operation of needle advancement and current control. Particularly, the needle is advanced by one hand while the current must be controlled by turning the knob 27 with the other hand, which is an extremely awkward operation for the user. Additionally, the nerve stimulator of the Chester patent restricts the size of the syringe upon which it may be mounted, thus, requiring the operator to change the syringe on the needle. This combination makes it very difficult to stabilize the needle within 1–2 mm of a nerve as desired for a regional block.

U.S. Pat. No. 5,306,236 to Blumenfeld et al. discloses a handle 36 to which the syringe, the needle and a conductor for carrying an electrical signal are attached. The control mechanism for controlling the application of current to the needle is located remotely from the needle at a stimulator device. Like the Chester patent, the system of Blumenfeld also does not allow for one-handed operation of both needle advancement and current control. Accordingly, the system of the Blumenfeld patent also provides a clumsy operation for the user.

It is frequently useful, during and after the performance of a regional anesthetic procedure, to know the depth at which the nerve structure was located. The consideration of needle tip depth is valuable both for medical record purposes as well as a check on needle position during the performance of a procedure. Accurate initial needle position may be obtained, but then undergo alteration by displacement during the injection portion of the procedure. Displacement may be due to inadvertent pressure applied by the operator, or the tendency of the injected fluid to force the needle back along its tissue track. The presence of visual guides on the needle itself, or a read out of needle tip depth on the nerve stimulator device, would provide feedback to the operator so as to prevent needle displacement. At present, there is no mechanism for providing such information with the currently available needles designed for use with nerve stimulators.

SUMMARY OF THE INVENTION

In accordance with the present invention, an output control needle comprising an insulated hypodermic needle having a means for fingertip control of the stimulator output current and a means of depth determination. The invention will provide a means for a single operator, the anesthetist, to accurately position a needle and perform a regional anesthetic technique without need of an assistant or excessive cabling. This further reduces the costs associated with an assistant's time while maintaining operating room hazards at a minimum.

It is an object of the present invention to provide a nerve stimulator needle with fingertip control of output current, which avoids the need for an assistant or foot pedal to adjust the output source during the performance of a regional anesthetic procedure.

It is an object of the present invention to provide a nerve stimulator needle with fingertip control of output current allowing the second hand to perform medication injection.

It is an object of the present invention to provide a nerve stimulator needle with a means of electronically measuring the depth at which a nerve structure is encountered.

It is an object of the present invention to provide a nerve stimulator needle with a means of visually measuring the depth at which a nerve structure is encountered.

In the present invention a nerve stimulator needle apparatus may comprise: a needle capable of carrying an electric current; a variable control mechanism which is operable to variably control the amplitude of an application of electric current to the needle; a plurality of electrical connectors connected to the variable control mechanism and the needle which allows the variable control mechanism to remotely connect to a nerve stimulation device which is operable to provide a voltage to the variable control mechanism and to provide a current pulse to the needle having an amplitude which is controlled by the variable control mechanism; and a housing which holds the variable control mechanism, the plurality of electrical connectors and the needle.

The needle may be an insulated hypodermic needle, and the apparatus may further comprise: an injection tube operably connected to the needle to provide a fluid to said needle. The housing may include a fluid path, and the injection tube may be connected to one end of the fluid path and the needle may be connected to another other end of said fluid path.

The variable control mechanism of the needle apparatus may include a pressure sensitive switching mechanism which changes the amplitude of the current applied to the needle in relation to the amount of pressure applied to the pressure sensitive switching mechanism.

The housing of the needle apparatus may further include conductive traces that connect the variable control mechanism and the needle to said electrical connectors.

The needle unit of the needle apparatus may include an electrically resistive layer covering the needle, wherein the resistance of the resistive layer changes with the length of the resistive layer, and a conductor associated with the housing may provide a voltage to the electrically resistive layer. The needle unit may further include an insulating layer between the electrically resistive layer and the needle.

The needle unit may further includes depth measurement marks that indicate the insertion depth of the needle.

The variable control mechanism of the needle apparatus may comprise a variable optical switching device. The variable optical switching device may include a partially colored plate and a fiber optic cable which directs light from a light source to impinge on the partially colored plate, and direct reflected light from the partially colored plate to a sensor. The partially colored plate preferably alters color or intensity component of the light impinged on it from said fiber optic cable in response to an application of pressure.

The variable optical switching device may include a graduated reflective plate and a fiber optic cable that directs light from a light source to impinge on the graduated reflective plate, and direct reflected light from the graduated reflective plate to a sensor. The graduated reflective plate preferably alters color or intensity component of the light impinged on it from the fiber optic cable in response to an application of pressure.

The invention may also include a nerve stimulator apparatus comprising: a nerve stimulator device comprising: a voltage source; a controller; and a current source operable to produce an electrical current in response to said controller; and a needle unit remotely located from said nerve stimulator device and connected to said nerve stimulator device only by at least one electrical conductor, said needle unit comprising: a variable control mechanism which is operable to receive a voltage from said voltage source and to provide instructions to said controller to variably control the amplitude of said electrical current provided by said current source; a needle capable of carrying said electric current from said current source having the amplitude controlled by said variable control mechanism; and a housing which holds said variable control mechanism and said needle.

The variable control mechanism may include a pressure sensitive switching mechanism that changes the amplitude of the current applied to the needle in relation to the amount of pressure applied to the pressure sensitive switching mechanism. The current source is preferably operable to increase or decrease current in response to the operation of the variable control mechanism, and the variable control mechanism is operable to increase or decrease current to the needle. The current source preferably changes the amplitude of the current in response to the operation of the variable control mechanism and the variable control mechanism is operable to control the rate of change of the current.

The needle unit may include an electrically resistive layer covering the needle, wherein the resistance of the resistive layer changes with the length of the resistive layer, and an electrical trace from an electrical connector provides a voltage from the voltage source, so as to maintain a constant current, to the electrically resistive layer. The microprocessor preferably determines the insertion depth of the needle according to the equation:

$$L_b = (R_t - R_a)/r_L$$

where $R_a$ is the resistance of the portion of the needle protruding above a skin surface of a subject; $R_t$ is the resistance of the total length of the needle; $r_L$ is the resistance per unit length of the needle; and $L_b$ is the insertion depth of the needle. Wherein the value $R_a$ is calculated from the ratio of the voltage of a signal detected by a return electrode attached to the surface of the skin of a subject divided by the applied current of the resistive layer on the needle.

The invention further comprises a method of locating nerves may comprise the steps of: (A) inserting a needle mounted on a housing through a surface of skin of a subject; (B) activating a variable control mechanism mounted on the housing to provide a variably controlled current to the needle; (C) monitoring a detected current signal from a return electrode attached to the surface of skin of a subject using a nerve stimulator device, wherein steps A and B are performed by the same hand of an operator.

The method of locating nerves may further comprise the step of determining the needle insertion depth by providing a voltage to a resistive layer, completing a circuit through a return electrode on the skin surface.

The step of determining the needle insertion depth is preferably performed according to the equation:

$$L_b = (R_t - R_a)/r_L$$

where $R_a$ is the resistance of the portion of the needle protruding above a skin surface of a subject; $R_t$ is the resistance of the total length of the needle; $r_L$ is the resistance per unit length of the needle; and $L_b$ is the insertion depth of the needle.

The determination of the needle depth may comprise the steps of: continuously applying a constant current to a resistive layer on the surface of the needle; periodically applying a current pulse to the needle while applying the constant current; waiting for a period of time to elapse after applying the current pulse to the needle and determining the resistance of the resistive layer of the needle exposed from the surface of skin of the subject; and calculating the depth of the needle inserted in the surface of skin of the subject.

BRIEF DESCRIPTION OF THE DRAWINGS

The accompanying drawings, which are incorporated in and form a part of the specification, illustrate the various embodiments of the present invention, and together with the description, serve to explain the principles of the invention. In the drawings.

DETAILED DESCRIPTION OF THE INVENTION

Reference will now be made in detail to the present preferred embodiment of the invention, an example of which is illustrated in the accompanying drawings.

Figure 1A:
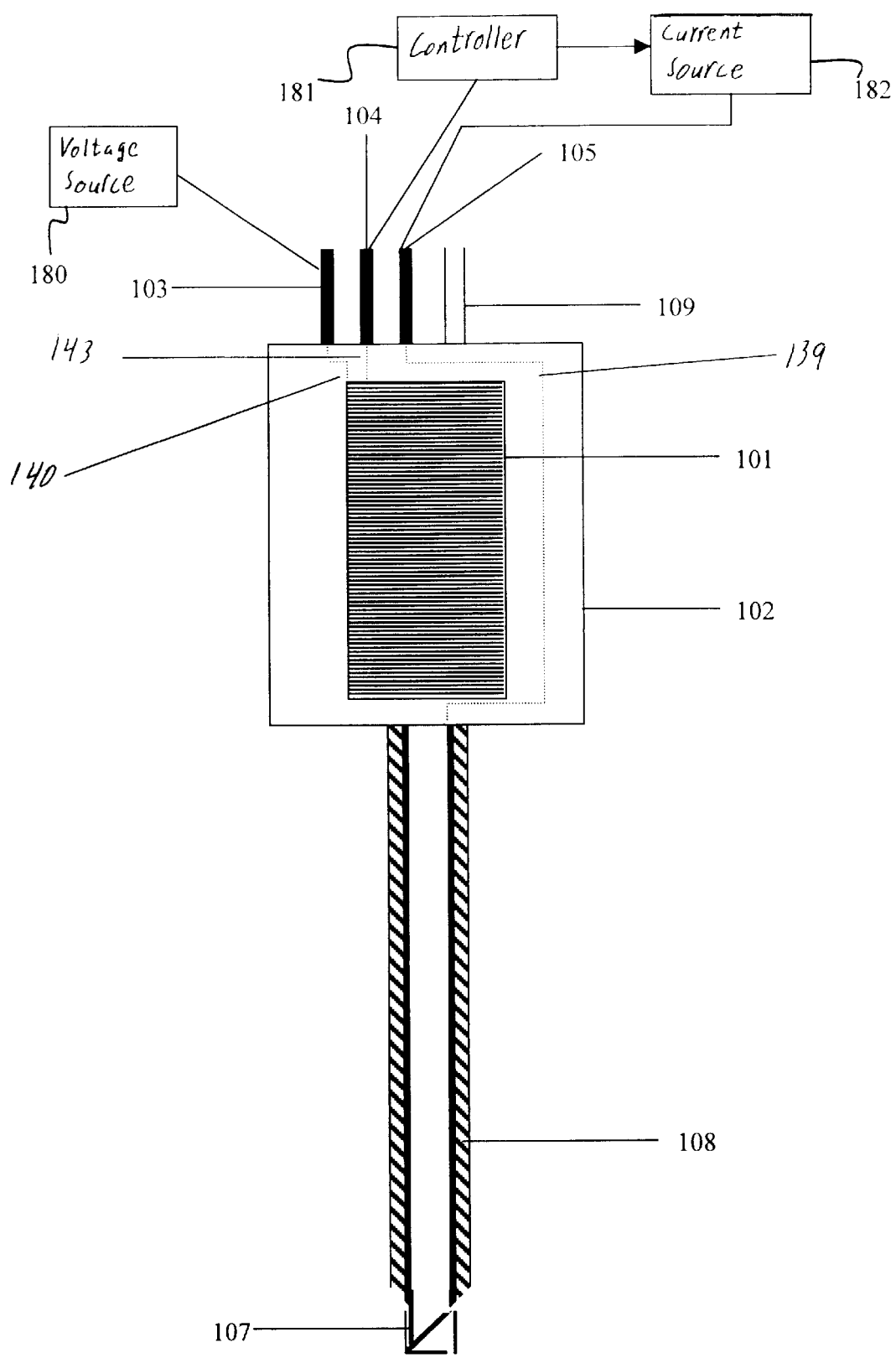
FIGS. 1A and 1B illustrate a first embodiment of stimulator needle assembly of the present invention.
Figure 1B:
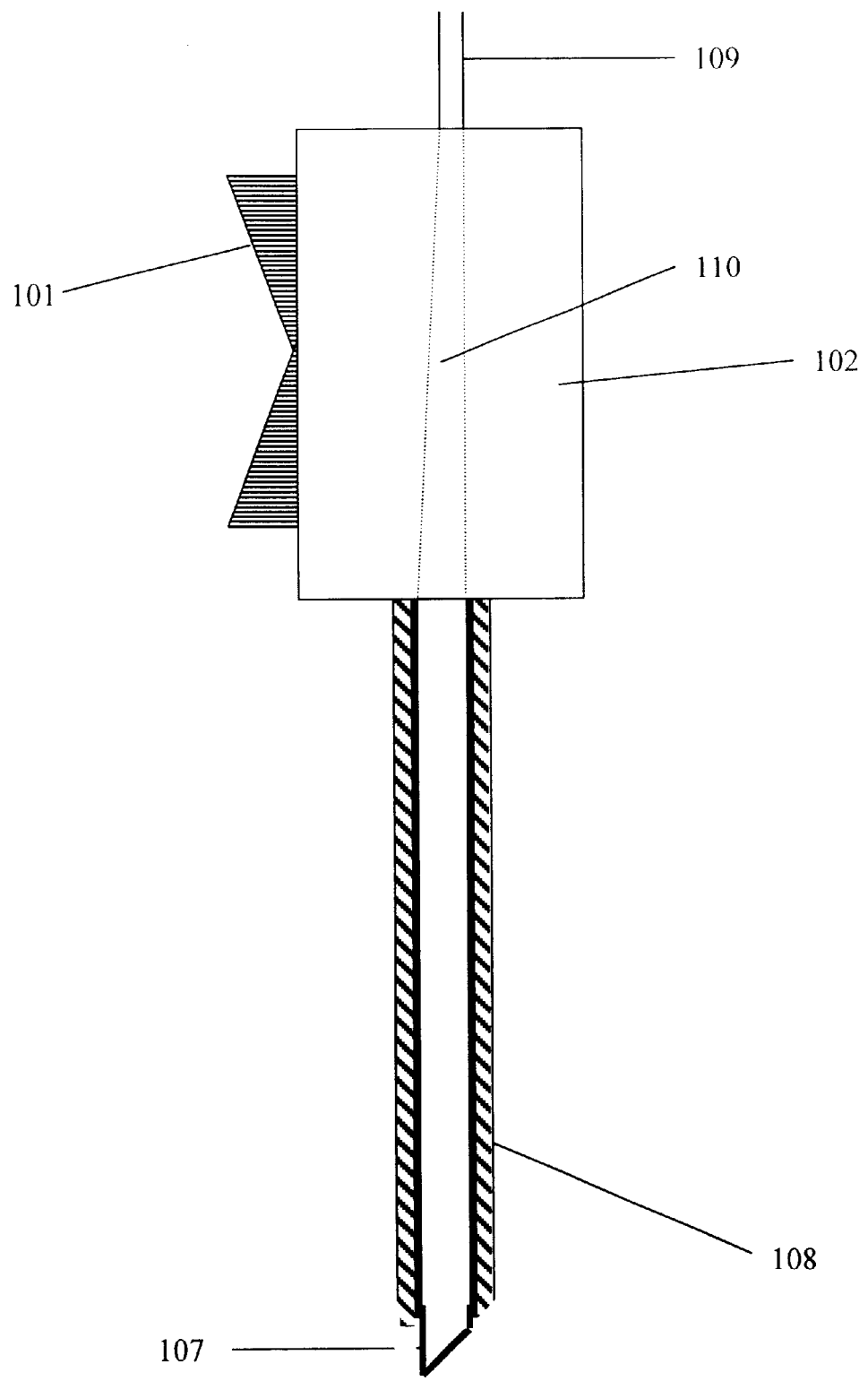

A preferred embodiment of the present invention comprises a nerve stimulator function that allows control of the current output through a fingertip control on the stimulating needle. A preferred embodiment of the needle assembly of the present invention is illustrated in FIG. 1A (front view) and FIG. 1B (side view). A needle assembly consists of a housing unit 102. The housing unit may be made of any suitable material such as molded plastic. The housing unit 102 preferably contains a plurality of electrical pin connectors 103, 104 and 105 that electrically connect the housing unit 102 to an external nerve stimulator device or a plurality of external devices. Electrical traces 139, 140, and 143 are preferably embedded within the housing unit 102 and are electrically connected to a corresponding electrical pin connector.

The housing unit 102 also preferably contains an embedded fluid path 110 through which fluid from a tube 109 may flow to a needle 107. The tube 109 may be any tube suitable for carrying fluids such as a plastic injection tube. The tube 109 may be formed within the housing unit 102 or may mate with the housing unit 102 via known techniques of mating tubes. Needle 107 is preferably inserted into a cavity (not shown) in the housing unit 102 so that it mates with the embedded fluid path 110. Needle 107 may be detachable from housing 102 or may be permanently affixed to housing 102. Those of skill in the art will appreciate that the tube 109 and the needle 107 should be attached to the embedded fluid path 110 according to techniques known in the art in a manner that avoids leakage of the fluid and also avoids contamination of the fluid. The hypodermic needle preferably consists of stainless steel, and is preferably coated with an insulation layer 108, although a needle without the insulation layer may be used but may provide less efficient current transfer to the nerve. The needle tip is preferably not coated with the insulation layer and the needle tip may be of any type of bevel, such as a short or a long bevel. The insulation layer 108 is preferably a biocompatible insulation layer and preferably comprised of Teflon, polyethylene, PVC, polypropylene, or any other suitable material.

A variable control mechanism 101 for variably controlling the current applied to needle 107 may include any type of finger actionable switch, such as a rocker switch, pressure switch, slider switch or any other known finger actionable switch, attached to the housing unit 102. A voltage may be applied from a voltage source 180 to the variable control mechanism 101 via an electrical pin connector 103 and electrical trace 140 in the housing unit 102 and reduced or increased depending on the operation of the variable control mechanism 101. The output voltage on the variable control mechanism 101 is directed to a control device 181, via a second electrical pin connector 104, for processing and determining the output current to be delivered from a current source 182 via the third electrical pin connector 105 to the embedded hypodermic needle 107. The current provided by the current source 182 is preferably in the form of a pulse train as known in the art.

Figure 2:
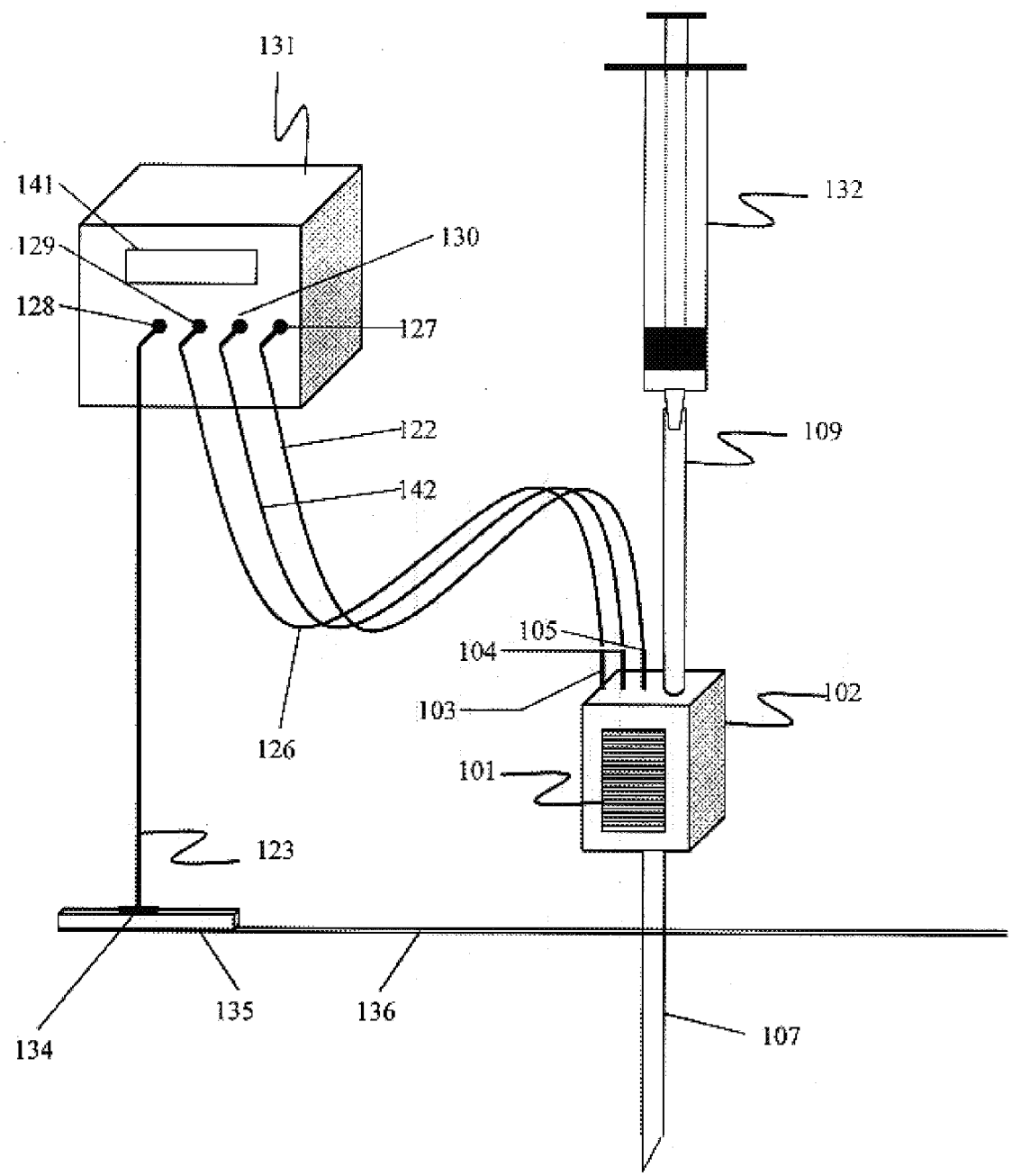
FIG. 2 illustrates the stimulator needle assembly of the first embodiment in operation.

FIG. 2 illustrates the operation of the stimulator needle assembly. As shown in FIG. 2, a syringe 132 is connected to housing unit 102 via tube 109. A hypodermic needle 107 is also attached to the housing unit 102, and advanced through the skin surface 136. A nerve stimulator device 131 is electrically connected to electrical pin connectors 103–105 via electrical cables 126, 142, and 122 through electrical pin connectors 129, 130 and 127, respectively. The source 180, control device 181 and the current source 182 are contained in the nerve stimulator 131.

Figure 3A:
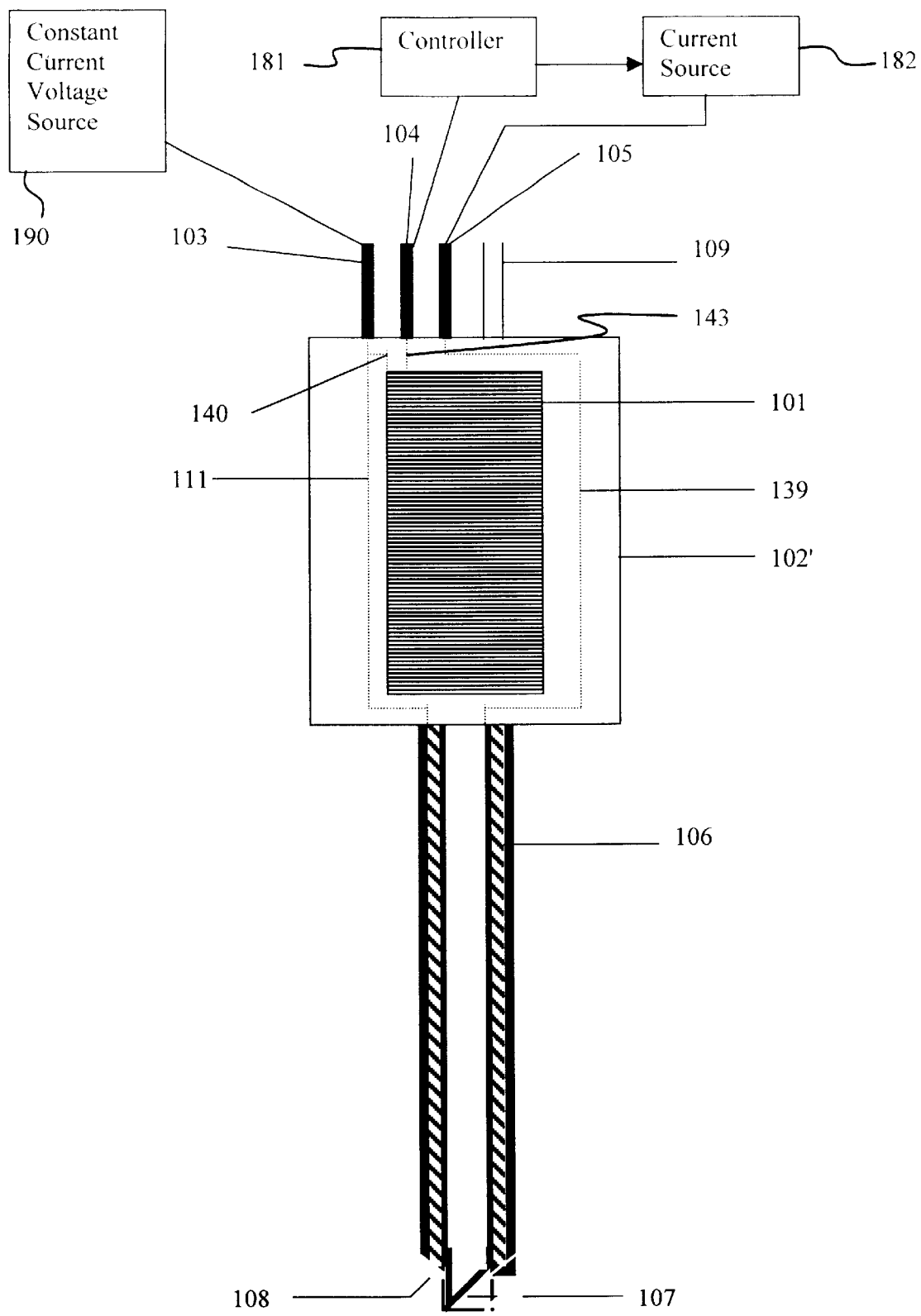
FIGS. 3A–3C illustrate a second embodiment of a stimulator needle assembly of the present invention.
Figure 3B:
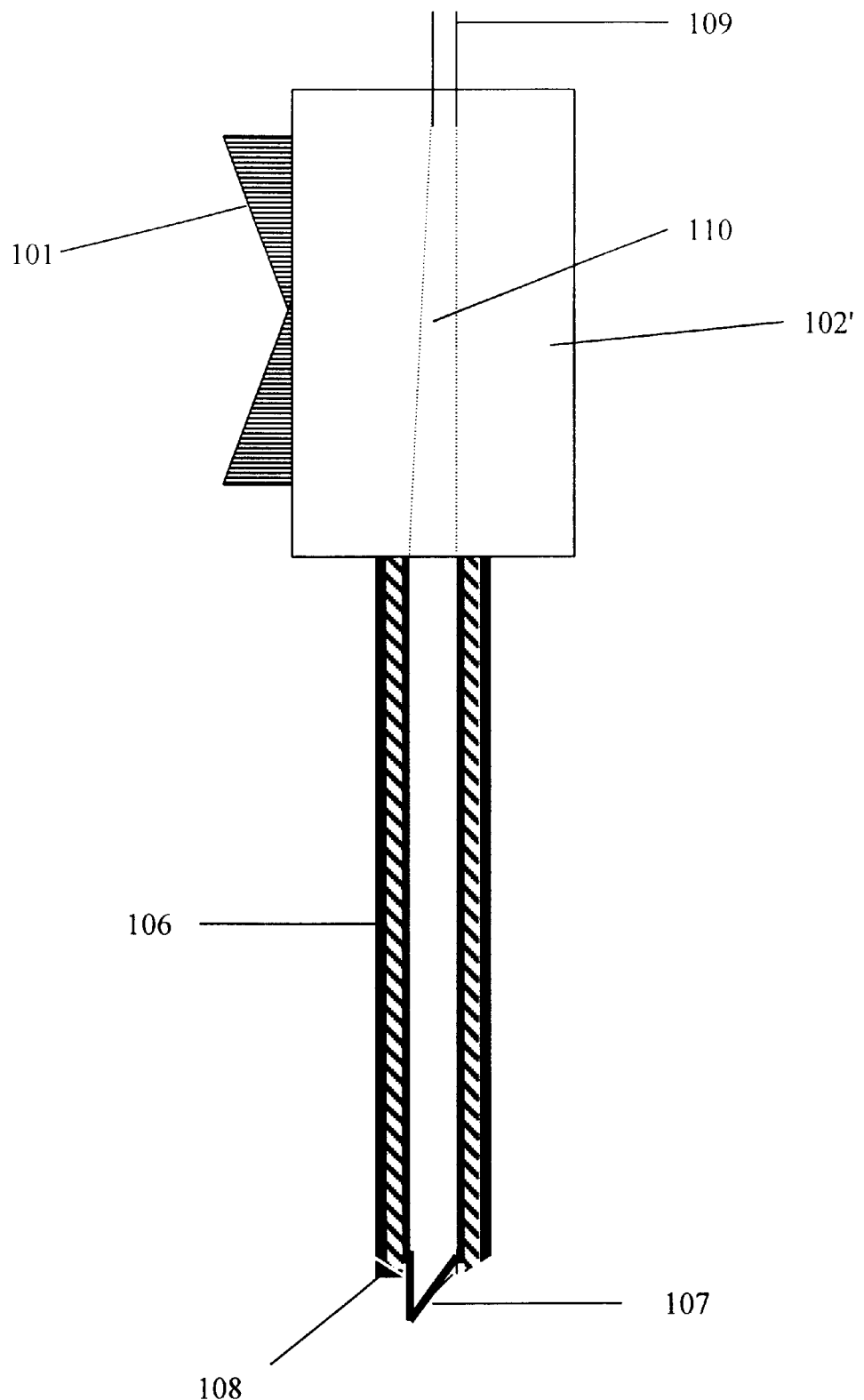
Figure 3C:
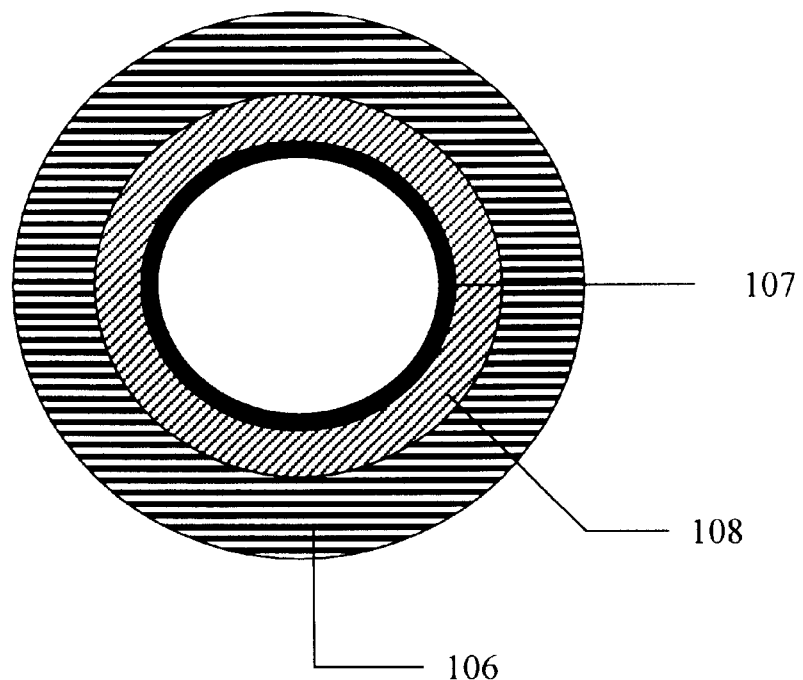

As the needle is advanced through the skin surface 136, the nerve stimulator 131 is activated and controlled by the variable control mechanism 101 via the current output control cable 142 attached to the nerve stimulator 131 by electrical pin connector 130. The output current is supplied through electrical pin connector 127 via an electrical cable 122 to electrical pin connector 105 on the housing unit 102. Voltage is output through electrical pin connector 129 via electrical cable 126 to electrical pin connector 103 on the housing unit 102 for output current control. The electrical return electrode 135 bears a connector 134 that attaches via an electrical cable 123 to an electrical pin connector 128 on the nerve stimulator 131. The return electrode 135 is typically a silver-silver chloride electrocardiographic electrode. The operator is able to determine the proximity of the needle tip to the nerve by observation of a visible twitch stimulated in the muscle supplied by the target nerve. In a nerve stimulator operation, current is supplied to the hypodermic needle 107 at a level of 1–2 mA and the needle advanced until muscle twitch is achieved. By following appropriate muscle twitches, the amplitude of the current output may be gradually decreased by the use of the variable control mechanism 101 until twitch is observed at less than 0.5 mA as shown on display 141. When the needle tip position is an appropriate distance from the nerve, e.g., 1–2 mm at a current output of less than 0.5 mA, the operator injects the solution in the syringe. This process, using a nerve stimulator needle of the prior art, is generally described in U.S. Pat. No. 5,830,151 to Hadzic et al. A second embodiment of the present invention is illustrated in FIGS. 3A, 3B and 3C. The second embodiment is similar to the first embodiment except that the second embodiment includes the ability to determine the depth of the needle inserted in the skin. The same components are numbered with the same reference numbers. FIG. 3A illustrates a frontal view of the second embodiment, FIG. 3B illustrates a side view, and FIG. 3C illustrates a cross sectional view of the needle of the second embodiment.

The needle 107 shown in FIGS. 3A, 3B and 3C is able to determine depth of hypodermic needle penetration beneath the skin by using a linear resistance coating 106 connected to the voltage source 180 via an electrical pin connector 103 and an electrical trace 111. The preferred material for this linear resistance coating is a conductive polymer coating such as a polyaniline (Ormecon™), although any suitable linear resistive material may be used, such as a normally nonconductive polymer that has been doped with a conductive material. For example, the nonconductive polymer silastic can be doped with carbon to become conductive. By controlling the amount of dopant, the resistance of the polymer may be adjusted to suitable levels. The linear resistance coating 106 is separated from the stainless steel hypodermic needle 107 by an insulation layer 108, shown as a hatched area surrounding the needle in the figures.

Figure 4:
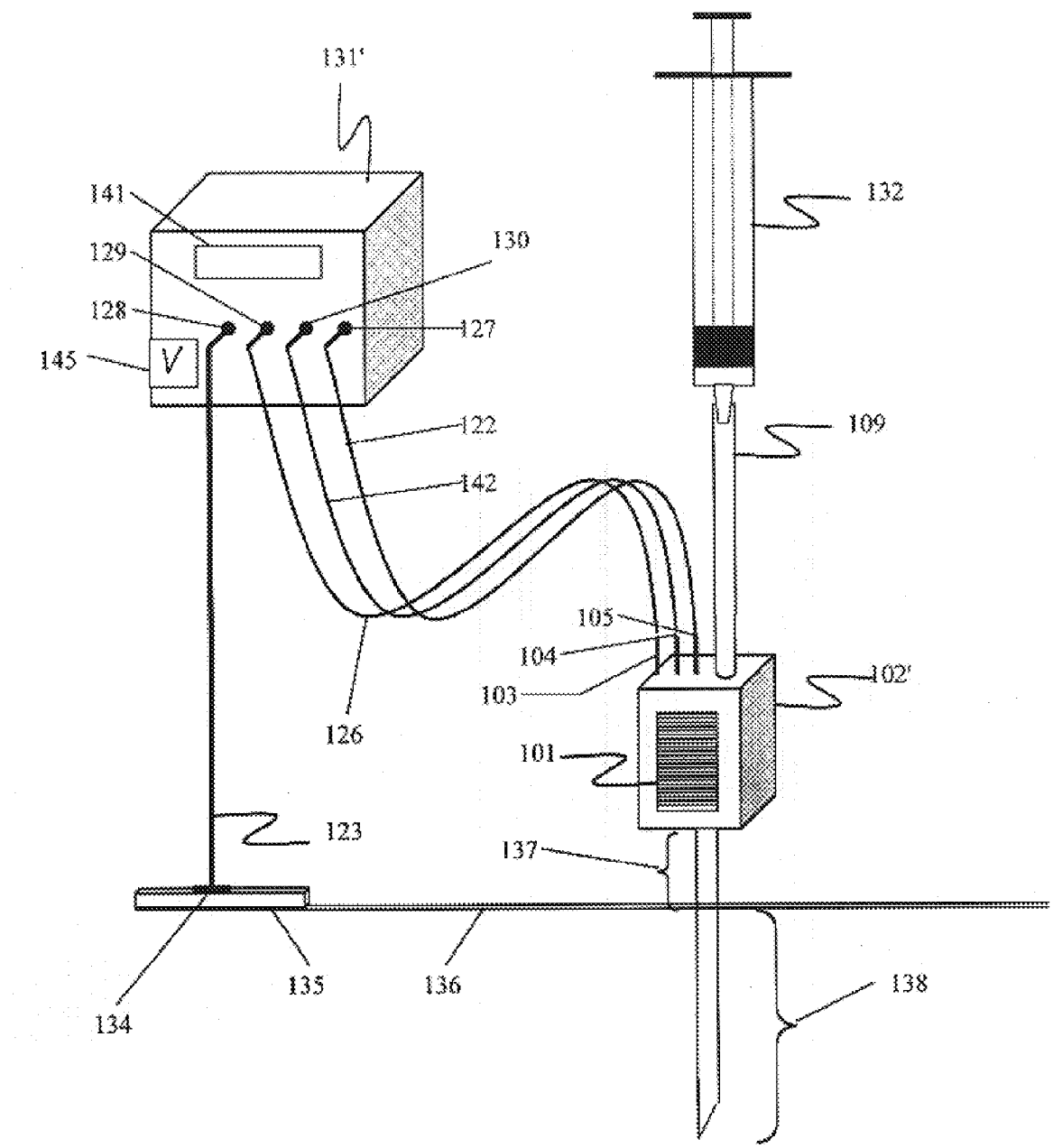
FIG. 4 illustrates the stimulator needle assembly of the second embodiment in operation.

The needle of the second embodiment also may be used with the nerve stimulator 131' shown in FIG. 4. The needle of the second embodiment locates a nerve in the same manner as described in the first embodiment, except that the needle of the second embodiment has the ability to determine the insertion depth of the needle in the skin of a subject. For this reason, nerve stimulator 131' in FIG. 4 contains a constant current voltage source 190.

Existing nerve stimulators are designed to deliver constant current pulses for nerve stimulation purposes. These devices do not provide constant current (a constant non pulsed current). However, one of skill in the art is able to readily design a constant current source 190, and the circuit design may be analogous to that for producing the constant current pulse for stimulation. The nerve stimulator 131' described herein preferably contains two separate current sources, one of which, the constant current source 182, is adjustable by the user for stimulation pulse generation, i.e. pulse current i. The other of which, the constant current voltage source 190, is not adjustable by the user and provides a constant current (I) to the linear resistance coating 106.

By way of example, as shown in FIG. 4, the return electrode 135 for depth determination by resistance measurement is located remotely on the skin surface and is the same return electrode as that for the current output of the nerve stimulator 131. In operation, a voltage signal from the constant current voltage source 190 is applied to the linear resistance coating 106 via electrical pin connector 103 and electrical trace 111. The circuit is completed through the linear resistance coating 106 as it penetrates the skin, thus the return electrode 135 detects the signal and provides the detected signal to the nerve stimulator 131' via electrical cable 123 and electrical pin connector 128. The nerve stimulator 131' detects the voltage of the detected signal using a voltmeter 145.

The resistance of the linear resistance coating 106 is constant per unit length and significantly higher than that of tissue, which is on the order of 1.0 megaohm per mm. Tissue impedance is typically in the range of 0.1–1.0 kilohms. Since the tissue impedance is less than the resistance of any portion of the needle by orders of magnitude, the resistance of the circuit is approximately that of the needle coating alone. The total resistance ($R_t$) of the needle linear resistance coating 106 is the product of the resistance per unit length ($r_L$) and the length of the needle ($L_t$). As the needle is advanced through the skin, $R_t$ may be represented as the sum of the length protruding above the skin ($L_a$) 137 multiplied by $r_L$ and of the length beneath the skin ($L_b$) 138 multiplied by $r_L$, as given in equation 1.

$$R_t = r_L \times L_t = (r_L \times L_a) + (r_L \times L_b) \qquad \text{Eq. 1}$$

Therefore, since the resistance determined by the nerve stimulator 131' in this circuit is directly related to the length of the coating that protrudes above the skin surface ($R_a = r_L \times L_a$), the length of the needle below the skin surface may be determined by equation 2.

$$L_b = (R_t - R_a)/r_L \qquad \text{Eq. 2}$$

where $R_a$ is the resistance of the portion of the needle protruding above the skin. Since $R_t$ and $r_L$ are known and $R_a$ is calculated directly from the ratio of the measured voltage to the applied current (Ohm's Law: V=IR), $L_b$ may be calculated. If the needle is inserted to the point that the housing unit 102 contacts the skin surface, $L_a=0$, the measured resistance is that of the tissue alone, and thus $L_b=L_t$ in that situation.

Figure 7:
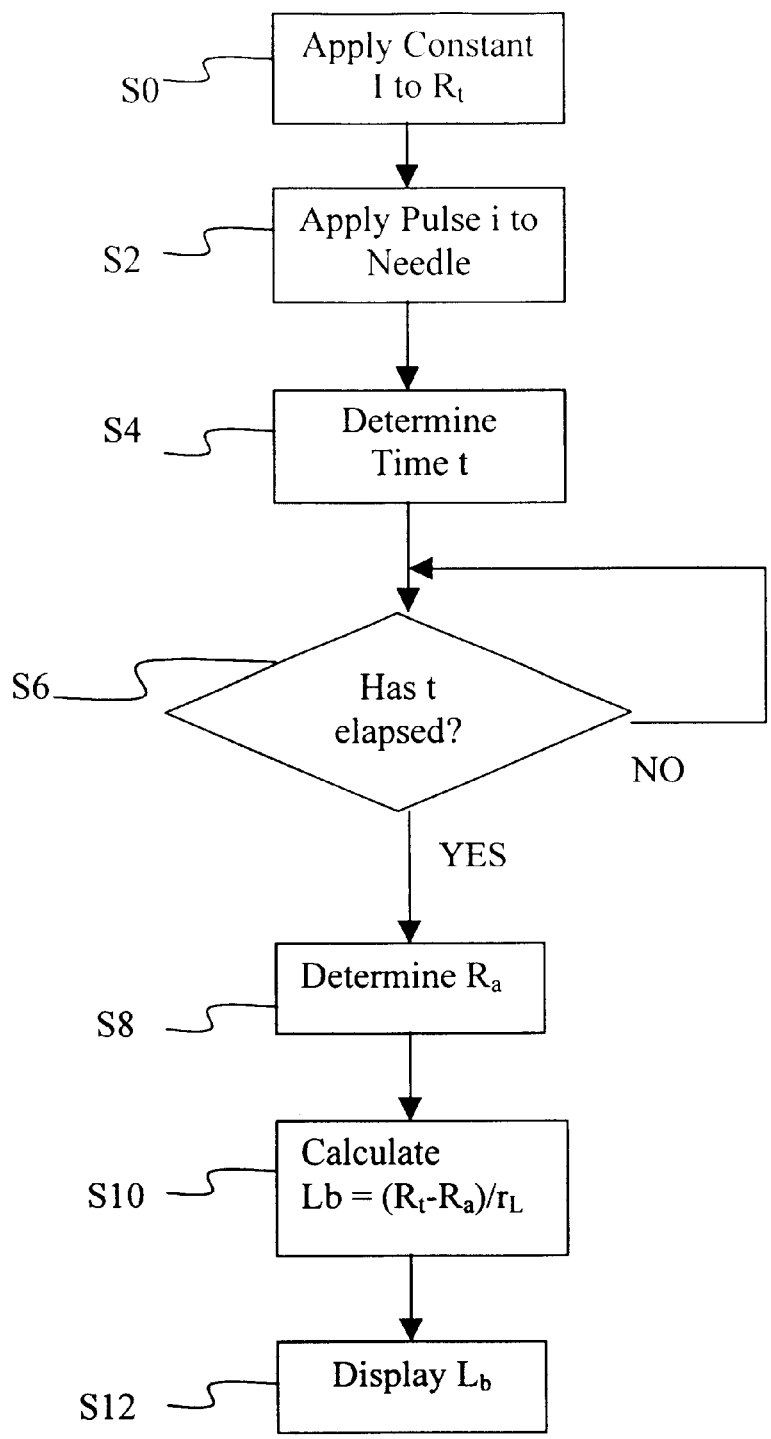
FIG. 7 is a flow diagram that illustrates the determination of the needle depth.

The return electrode 135 is used for both stimulator current control and for needle depth determination through the measurement of resistance. FIG. 7 illustrates an exemplary method of determining the depth of the needle which is preferably carried out by a microprocessor in the nerve stimulator 131'. As shown in step S0, the nerve stimulator 131' illustrated in FIG. 4 provides a constant DC current I, by way of a variable voltage, to the linear resistive coating 106 on the nerve stimulator needle 107 via electrical pin connector 103 and electrical trace 111. The nerve stimulator 131' provides a periodic current pulse i to the needle 107, having its amplitude controlled by variable control mechanism 101, via electrical trace 139 (step S2). The constant current I is preferably continuously provided, and is not interrupted by the periodic current pulse i provided to the needle 107. The resistance $R_a$ is determined from the DC current I after the current pulse i decays in the skin of the subject, i.e. during the portion of the interpulse interval when no current pulse from the stimulator function is occurring. The resistance measurement cannot occur early in the interpulse interval due to capacitive functions of the skin which result in a discharge voltage according to the relationship $V = V_i \times e^{(-t/RC)}$, where V is the observed voltage, $V_i$ is the applied voltage of the current pulse i on needle 107, t is the elapsed time, and RC is the product of the resistance and the capacitance of the skin. Consequently, the resistance measurements for depth determination are collected in a timed fashion, rather than continuously. For example, in the preferred embodiment, the current pulse is less than or equal to 5 msec in duration and, since the frequency of the pulse signal provided to the nerve stimulator needle 107 is a maximum of 5 Hz, the interpulse duration is 45 msec.

In step S4, the microprocessor determines the decay time t of the current pulse in the skin of the subject as t=5RC. Particularly, for a circuit containing a parallel resistance (R) and capacitance (C), such as biological tissue, a tissue time constant may be calculated from the product of R and C. When subjected to a current pulse, the capacitive element of such a circuit charges over a defined time interval. On termination of the current pulse, this capacitive element discharges over a characteristic time interval, which follows an exponential decay curve, which takes about five tissue time constants (5RC) to reach 99% of the final value. This is described in more detail by Nunn (Nunn J F, Applied Respiratory Physiology, Butterworths, London, 1977, pg. 464–469) and Horowitz and Hill (Horowitz P and Hill W, The Art of Electronics, Cambridge University Press, Cambridge, Mass., 1986, pg.20–21). Since tissue time constants are in the range of 1 msec or less, allowing greater than 5 msec to pass following the termination of the stimulating pulse provides adequate time for the measured voltage to approximate baseline values of the voltage applied to the resistive layer. Alternatively, t may set to a value greater than or equal to 5 msec.

At step S6, the microprocessor waits for the time t to elapse since the end of the current pulse i (No in step 6). Once the time t has elapsed (Yes in step 6), the measured voltage from return electrode 135 via voltmeter 145 is used to calculate $R_a$ (step S8). The needle depth $L_b$ is then calculate in step S10 according to equation 2, and displayed in step S12. The calculated value of $L_b$ may then be visually displayed on display 141. Those of skill in the art will appreciate that the calculated value $L_b$ may also be audibly displayed and/or may be printed by a printing device attached either directly or indirectly to nerve stimulator 131'.

Figure 5:
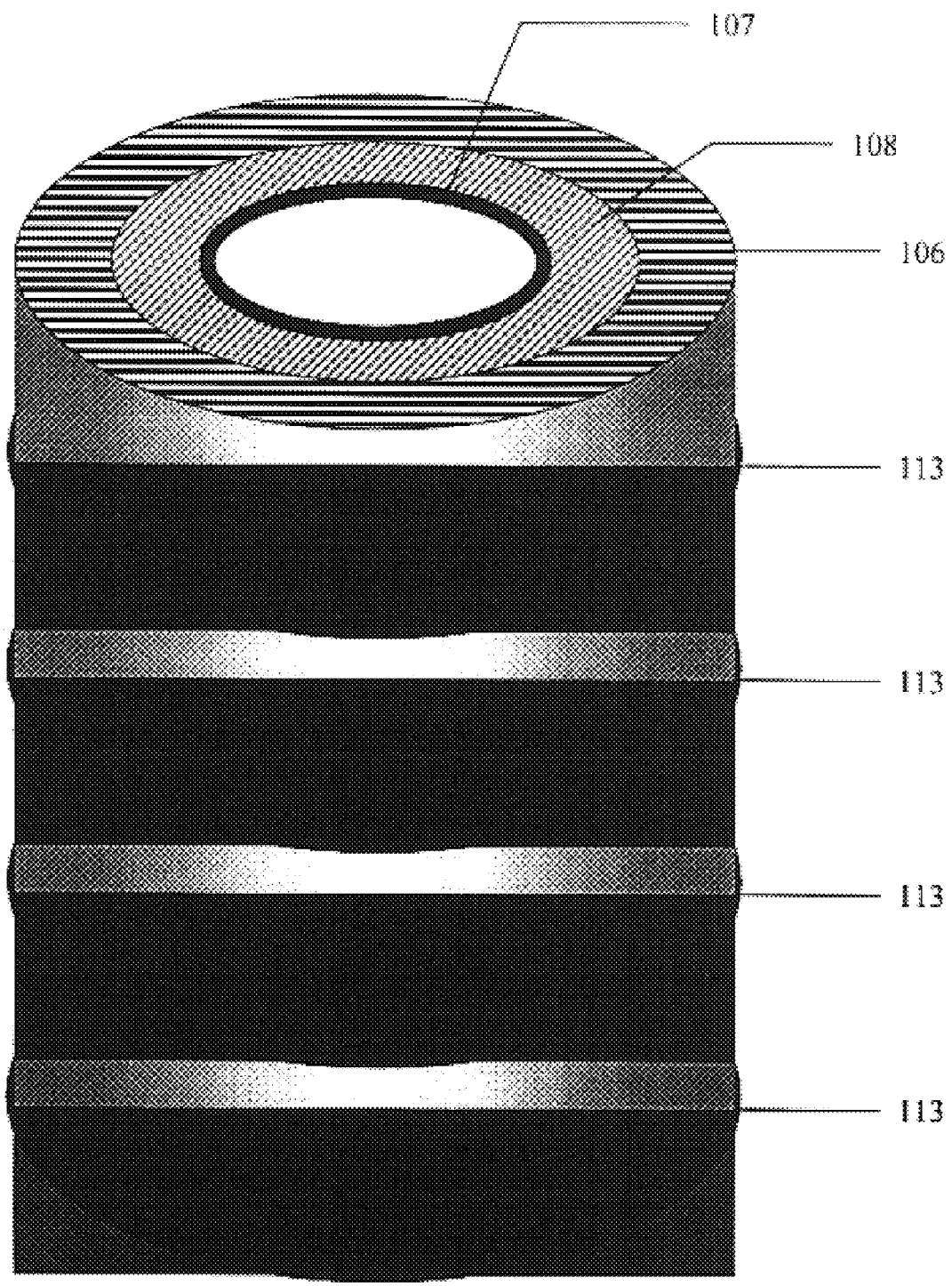
FIG. 5 illustrates a modified version of the needle shaft of the second embodiment.

FIG. 5 illustrates a cross section of the needle that may be used with the second embodiment. As illustrated in FIG. 5, needle 107 is coated with insulation layer 108 that is coated with linear resistive coating 106 as in the second embodiment. In FIG. 5, indelible marks 113, preferably comprised of biocompatible material, may be included on the resistance coating to provide visual reference of the depth to which the tip of the needle has been inserted. These depth measuring mechanisms allow accurate recording of the needle depth at which an injection was performed and allow for accurate maintenance of needle position during the injection procedure as well as for a period of time after injection when subsequent stimulation attempts are undertaken by the anesthetist. It will be appreciated that the indelible marks 113 may be applied to the insulation layer 108, in the absence of the resistive coating 106, to provide a visual depth reference.

Figure 6:
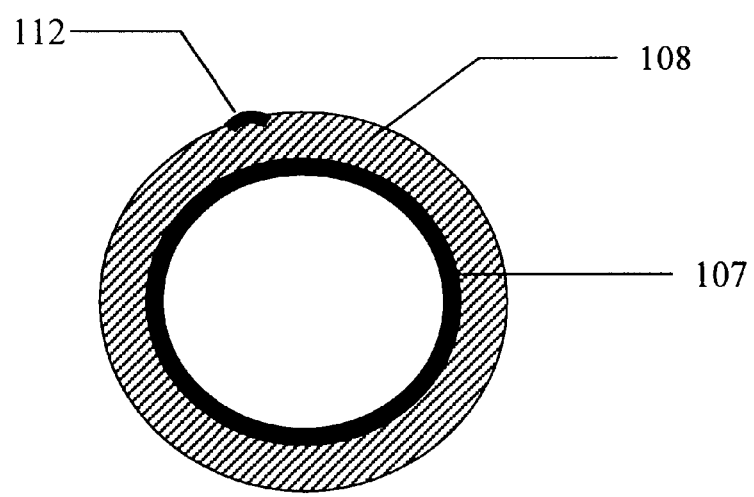
FIG. 6 illustrates a third embodiment of a stimulator needle assembly of the present invention.

A third embodiment is shown in FIG. 6. In this embodiment, a strip of resistance material 112, such as a tantalum wire, or ceramic strip resistance, may be substituted for the conductive polymer. This material preferably runs the length of the needle shaft and is separated from the hypodermic needle 107 by the insulation layer 108. This material provides the same linear resistance characteristics as the conductive polymer for use in depth determination, and operates in the same manner as described in embodiment 2.

Figure 8:
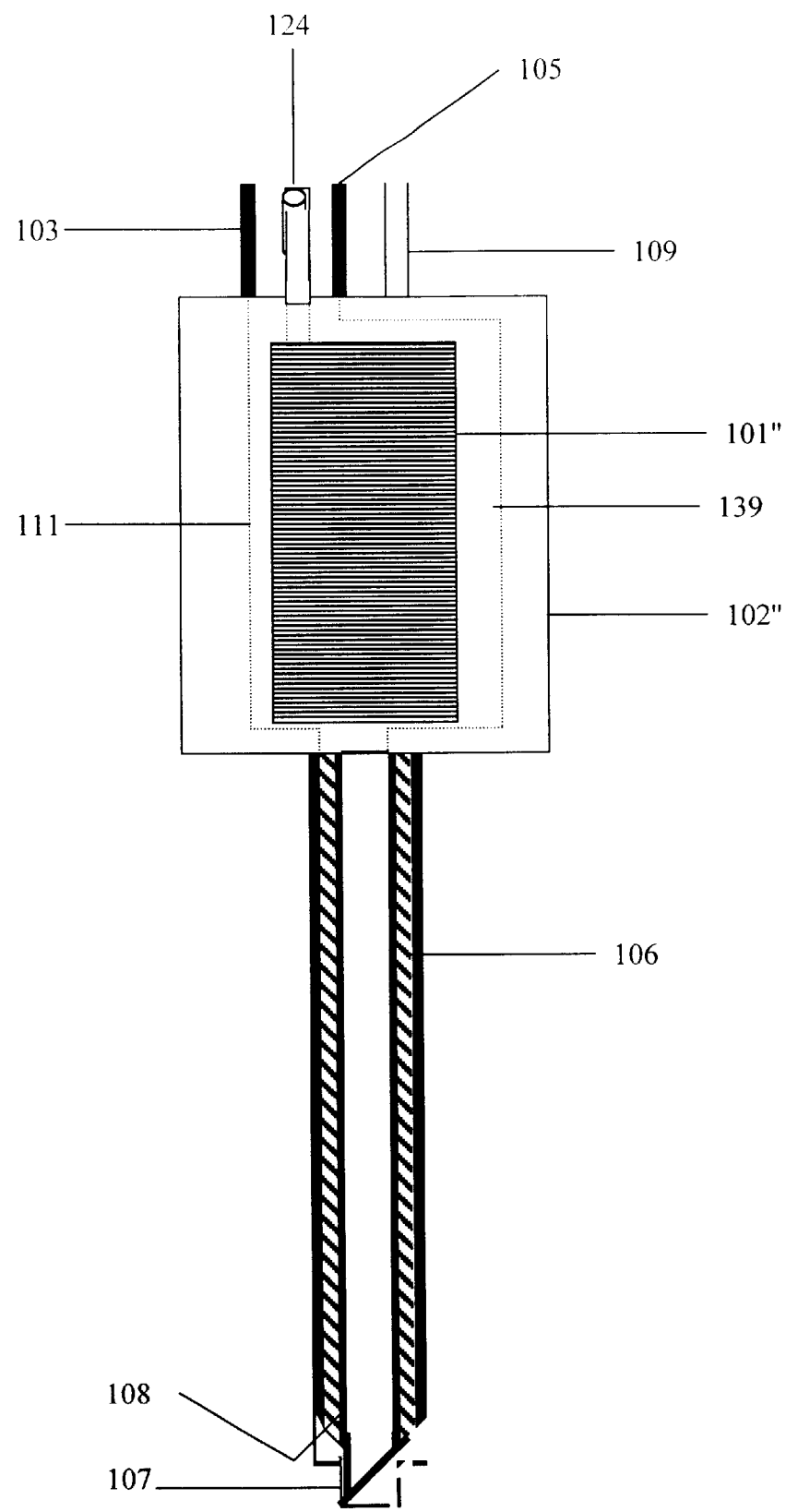
FIG. 8 illustrates a fourth embodiment of a stimulator needle of the present invention.
Figure 9:
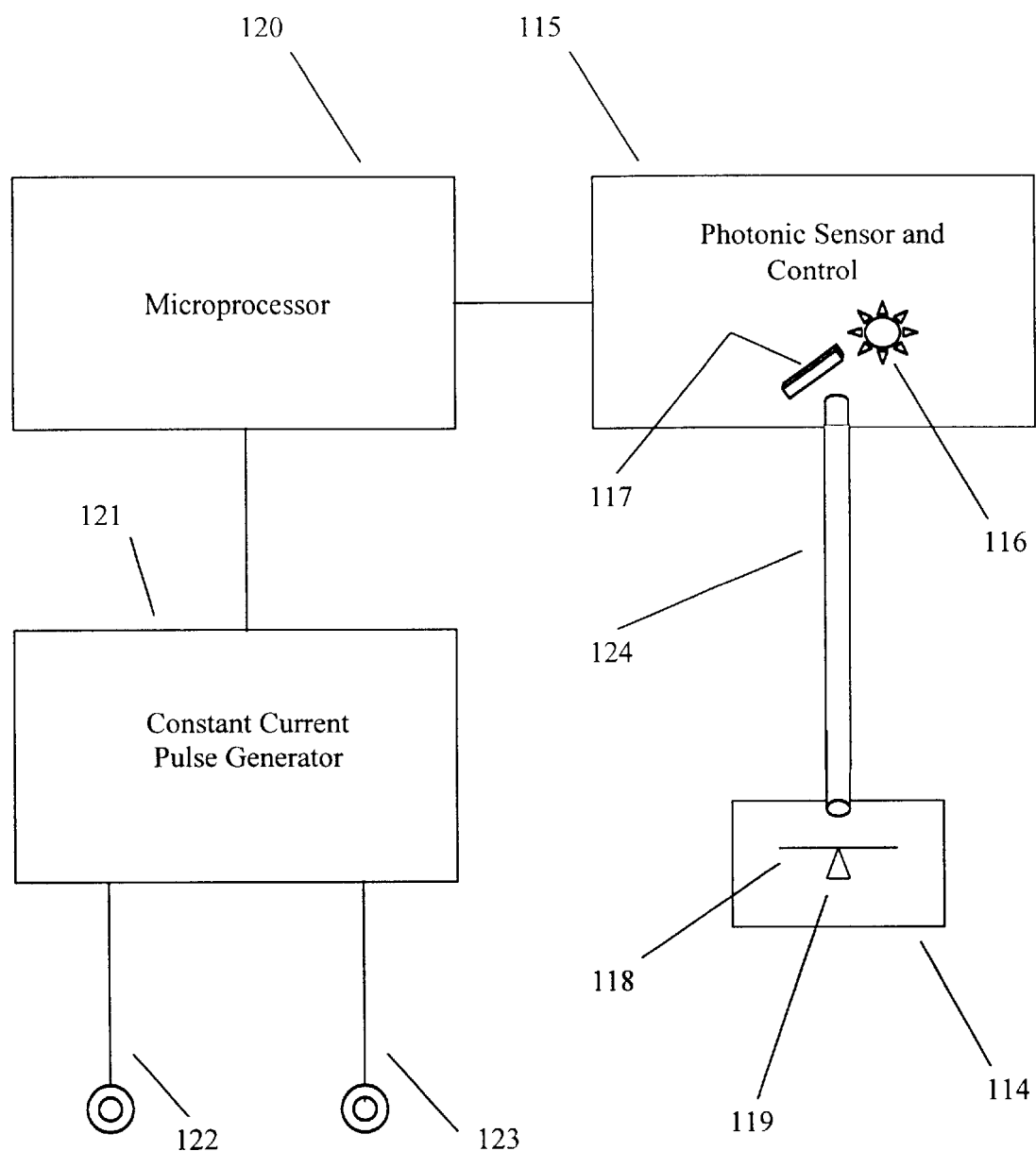
FIG. 9 illustrates the operation of the variable control mechanism of the fourth embodiment of the present invention.

A fourth embodiment of the invention is illustrated in FIGS. 8 and 9. In this embodiment, the variable control mechanism 101" may be an optical device controlling the current output by a mixture of light wavelengths determined by the degree to which the variable control mechanism 101 is depressed. An example of such a control device is the Coldswitch™. In the case of optical control, the electrical pin connector 104 is replaced by a fiber optic cable 124. The same elements in this embodiment as in the previous embodiments are numbered the same. Just as in the first embodiment, the variable control mechanism 101" is preferably connected to a nerve stimulator 131 or 131' that senses the direction of change mediated through the variable control mechanism 101", as well as the rate of change of switching events.

The operation of this embodiment is illustrated in FIG. 9. In FIG. 9, light from an LED source 116 contained in a photonic sensor and control 115 is directed via fiber optic cable 124 to an optical control mechanism 114, contained in the variable control mechanism 101". Optical control mechanism 114 contains a reflective plate 118 that is partially colored, such as by a color coating, or is a graduated reflective plate that has different reflective properties along the length of the plate. Optical control mechanism 114 also contains a pivot 119 upon which reflective plate 118 may pivot upon the application of pressure from an operator. The light from LED source 116 is reflected off of reflective plate 118 and transmitted back to the photonic sensor 117 via fiber optic cable 124. The photonic sensor and control 115 detects the direction of change of variable control mechanism 101", mediated through the optical control mechanism 114, as well as the rate of change of switching events, by the reflected color or intensity mixing. Color or intensity mixing is accomplished by a reflective plate 118. When the reflective plate 118 is rocked by finger pressure on its pivot 119, the white incident light emitted from the fiber optic cable 124 is reflected back with altered color or intensity components. The intensity or color is detected by the photonic sensor 117, electronically processed by the microprocessor 120 and converted to a corresponding current output via the constant current pulse generator 121. The current output is directed to the stimulating needle electrical pin connector 105 by an electrical cable 122 with the return supplied by a second electrical cable 123 to the return electrode 135 located remotely on the skin surface. Just as in the first embodiment, commands to the nerve stimulator can be controlled through switching events, including, but not limited to sequential taps, sudden release or sudden depression.

The foregoing description of a preferred embodiment of the invention has been presented for purposes of illustration and description. It is not intended to be exhaustive or to limit the invention to the precise form disclosed, and obviously many modifications and variations are possible in light of the above teaching. For example, although the method of FIG. 7 is described as being performed by a microprocessor, the method may be performed by a hard wired system or any other suitable processing system. Additionally, the terms electrical traces and electrical cables is are considered to encompass any type of known electrical conductors, such as, but not limited to metallic wires or non metallic electrical conductors, which may be embedded or non-embedded, and which may be coated with an insulator or non-coated.

What is claimed is:

1. A nerve stimulator needle apparatus comprising:
 a needle capable of carrying an electric current;
 a variable control mechanism which is operable to variably control the amplitude of an application of electric current to said needle during a procedure using said needle;
 a plurality of electrical connectors connected to said variable control mechanism and said needle which allows said variable control mechanism to remotely connect to a nerve stimulation device which is operable to provide a voltage to said variable control mechanism and to provide a current pulse to said needle having an amplitude which is controlled by said variable control mechanism; and a housing which holds said variable control mechanism, said plurality of electrical connectors and said needle, wherein an electrically resistive layer covers said needle, the resistance of said resistive layer changes with the length of said resistive layer, and an electrical trace from an electrical pin connector provides a voltage to said electrically resistive layer from said nerve stimulator device.

2. The nerve stimulator needle apparatus of claim 1, wherein said needle is a hypodermic needle, said apparatus further comprising:

an injection tube operably connected to said needle to provide a fluid to said needle.

3. The nerve stimulator needle apparatus of claim 2, wherein said housing includes a fluid path, and said injection tube is connected to one end of said fluid path and said needle is connected to another other end of said fluid path.

4. The nerve stimulator needle apparatus of claim 1, wherein said variable control mechanism includes a pressure sensitive switching mechanism which changes the amplitude of said current applied to said needle in relation to the amount of pressure applied to said pressure sensitive switching mechanism.

5. The nerve stimulator needle apparatus of claim 1, wherein said variable control mechanism is operable to increase or decrease current to the needle.

6. The nerve stimulator needle apparatus of claim 1, wherein said variable control mechanism is operable to control a rate of change of the current.

7. The nerve stimulator needle apparatus of claim 1, wherein said housing further includes conductive traces which connect said variable control mechanism and said needle to said electrical connectors.

8. The nerve stimulator needle apparatus of claim 1, wherein the variable control mechanism is operable to variably control the amplitude of an application of electric current to said needle during a procedure using said needle on a subject based on feedback from the subject.

9. The nerve stimulator needle apparatus of claim 1, wherein said needle further includes an insulating layer between said electrically resistive layer and said needle.

10. A nerve stimulator needle apparatus comprising:

a needle capable of carrying an electric current;

a variable control mechanism which is operable to variably control the amplitude of an application of electric current to said needle during a procedure using said needle;

a plurality of electrical connectors connected to said variable control mechanism and said needle which allows said variable control mechanism to remotely connect to a nerve stimulation device which is operable to provide a voltage to said variable control mechanism and to provide a current pulse to said needle having an amplitude which is controlled by said variable control mechanism; and a housing which holds said variable control mechanism, said plurality of electrical connectors and said needle, wherein said needle further includes an insulating layer between an electrically resistive layer and said needle.

11. A nerve stimulator apparatus comprising:

a nerve stimulator device comprising:
a voltage source;
a controller; and
a current source operable to produce an electrical current in response to said controller; and a needle unit remotely located from said nerve stimulator device and connected to said nerve stimulator device only by at least one electrical conductor, said needle unit comprising:

a variable control mechanism which is operable to receive a voltage from said voltage source and to provide instructions to said controller to variably control the amplitude of said electrical current provided by said current source during a procedure using said needle unit;

a needle capable of carrying said electric current from said current source having the amplitude controlled by said variable control mechanism; and a housing which holds said variable control mechanism and said needle, wherein said needle unit includes an electrically resistive layer covering said needle, wherein the resistance of said resistive layer changes with the length of said resistive layer, and an electrical trace from an electrical connector provides a voltage from said voltage source to said electrically resistive layer.

12. The nerve stimulator apparatus of claim 11, wherein said needle is a hypodermic needle, said apparatus further comprising:

an injection tube operably connected to said needle to provide a fluid to said needle.

13. The nerve stimulator apparatus of claim 12, wherein said housing includes a fluid path, and said injection tube is connected to one end of said fluid path and said needle is connected to another other end of said fluid path.

14. The nerve stimulator apparatus of claim 11, wherein said variable control mechanism includes a pressure sensitive switching mechanism which changes the amplitude of said current applied to said needle in relation to the amount of pressure applied to said pressure sensitive switching mechanism.

15. The nerve stimulator apparatus of claim 11, wherein said current source is operable to increase or decrease current in response to the operation of said variable control mechanism, and said variable control mechanism is operable to increase or decrease current to the needle.

16. The nerve stimulator apparatus of claim 11, wherein the current source changes the amplitude of said current in response to the operation of said variable control mechanism and said variable control mechanism is operable to control the rate of change of the current.

17. The nerve stimulator apparatus of claim 11, further comprising electrical connectors mounted to said housing, wherein the electric current is provided through said electrical connectors.

18. The nerve stimulator apparatus of claim 17, wherein said housing further includes conductive traces which connect said variable control mechanism and said needle to said electrical connectors.

19. The nerve stimulator apparatus of claim 11, wherein said needle unit further includes an insulating layer between said electrically resistive layer and said needle.

20. The nerve stimulator apparatus of claim 11, wherein said controller includes a microprocessor, and said microprocessor determines the insertion depth of the needle according to the equation:

$$L_b = (R_t - R_a) / r_L$$

where $R_a$ is the resistance of the portion of the needle protruding above a skin surface of a subject;

$R_t$ is the resistance of the total length of the needle;

$r_L$ is the resistance per unit length of the needle; and $L_b$ is the insertion depth of the needle.

21. The nerve stimulator apparatus of claim 20, wherein the value $R_a$ is calculated from the ratio of the applied voltage to the resistive layer on the needle divided by the current detected by a return electrode attached to the surface of the skin of a subject.

22. The nerve stimulator apparatus of claim 11, wherein the variable control mechanism is operable to variably control the amplitude of an application of electric current to said needle during a procedure using said needle on a subject based on feedback from the subject.

23. A nerve stimulator apparatus comprising:
   a nerve stimulator device comprising:
   a voltage source;
   a controller; and
a current source operable to produce an electrical current in response to said controller: and
   a needle unit remotely located from said nerve stimulator device and connected to said nerve stimulator device only by at least one electrical conductor, said needle unit comprising:
      a variable control mechanism which is operable to receive a voltage from said voltage source and to provide instructions to said controller to variably control the amplitude of said electrical current provided by said current source during a procedure using said needle unit;
      a needle capable of carrying said electric current from said current source having the amplitude controlled by said variable control mechanism; and
      a housing which holds said variable control mechanism and said needle,
      wherein said needle unit further includes an insulating layer between an electrically resistive layer and said needle.

24. A method of locating nerves comprising the steps of:
   (A) inserting a needle mounted on a housing through a surface of skin of a subject;
   (B) activating a variable control mechanism mounted on said housing to provide a variably controlled current to said needle during a procedure using said needle;
   (C) monitoring a detected current signal from a return electrode attached to said surface of skin of a subject using a nerve stimulator device; and
   (D) determining the needle insertion depth by providing a voltage to a resistive layer, completing a circuit through a return electrode on the skin surface.

wherein steps A and B are substantially performed simultaneously by the same hand of an operator.

25. The method of locating nerves according to claim 24, wherein the step of determining the needle insertion depth is performed according to the equation:

$$L_b = (R_t - R_a) / r_L$$

where $R_a$ is the resistance of the portion of the needle protruding above a skin surface of a subject;

$R_t$ is the resistance of the total length of the needle;

$r_L$ is the resistance per unit length of the needle; and $L_b$ is the insertion depth of the needle.

26. The method of locating nerves according to claim 25, wherein the value $R_a$ is calculated from the ratio of the applied voltage to the resistive layer on the needle divided by the current detected by the return electrode attached to the surface of the skin of a subject.

27. The method of locating nerves according to claim 24, wherein the step of activating a variable control mechanism to provide a variably controlled current to said needle variably controls the current to said needle based on feedback from the subject.

28. A method of locating nerves comprising the steps of:
   (A) inserting a needle mounted on a housing through a surface of skin of a subject;
   (B) activating a variable control mechanism mounted on said housing to provide a variably controlled current to said needle during a procedure using said needle;
   (C) monitoring a detected current signal from a return electrode attached to said surface of skin of a subject using a nerve stimulator device,
   wherein steps A and B are substantially performed simultaneously by the same hand of an operator and
   wherein the determination of the needle depth comprises the steps of:
      continuously applying a constant current to a resistive layer on the surface of said needle;
      periodically applying a current pulse to said needle while applying said constant current;
      waiting for a period of time to elapse after applying said current pulse to said needle and determining the resistance of the resistive layer of said needle exposed from the surface of skin of the subject; and
      calculating the depth of said needle inserted in the surface of skin of the subject.

* * * * *